US011937878B2

(12) United States Patent
Wei et al.

(10) Patent No.: US 11,937,878 B2
(45) Date of Patent: Mar. 26, 2024

(54) SYSTEMS AND METHODS FOR HIGH DYNAMIC RANGE OPTICAL COHERENCE TOMOGRAPHY ANGIOGRAPHY (HDR-OCTA)

(71) Applicant: Oregon Health & Science University, Portland, OR (US)

(72) Inventors: Xiang Wei, Portland, OR (US); Yali Jia, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 638 days.

(21) Appl. No.: 17/098,152

(22) Filed: Nov. 13, 2020

(65) Prior Publication Data

US 2021/0145277 A1 May 20, 2021

Related U.S. Application Data

(60) Provisional application No. 62/937,098, filed on Nov. 18, 2019.

(51) Int. Cl.
*A61B 3/12* (2006.01)
*A61B 3/10* (2006.01)
*G06T 5/00* (2006.01)
*G06T 5/50* (2006.01)

(52) U.S. Cl.
CPC ............ *A61B 3/1233* (2013.01); *A61B 3/102* (2013.01); *G06T 5/009* (2013.01); *G06T 5/50* (2013.01); *G06T 2207/10101* (2013.01); *G06T 2207/20221* (2013.01); *G06T 2207/30041* (2013.01); *G06T 2207/30104* (2013.01)

(58) Field of Classification Search
CPC ...................... A61B 3/102; G06T 5/50; G06T 2207/10101; G06T 2207/20221
See application file for complete search history.

(56) References Cited

U.S. PATENT DOCUMENTS

2018/0055355 A1* 3/2018 Sarunic ............... A61B 3/1241

OTHER PUBLICATIONS

"Wide dynamic range high-speed three-dimensional quantitative OCT angiography with a hybrid-beam scan" by T. Park et al. Optics Letters. vol. 43, No. 10. May 2018. 2237-2240 (Year: 2018).*
"High-dynamic range microscope imaging based on exposure bracketing in full-field optical coherence tomography" by A. Leong-Hoi et al. Optics Letters. vol. 41, No. 7. Apr. 2016. 1313-1316 (Year: 2016).*

* cited by examiner

*Primary Examiner* — Jason M Ip
(74) *Attorney, Agent, or Firm* — Schwabe, Williamson & Wyatt, P.C.

(57) ABSTRACT

Disclosed herein are methods and systems for optical coherence tomography (OCT) angiography (OCTA). An interleaved scanning pattern is described herein for both raster and bidirectional scanning methods. The interleaved scanning pattern provides B-scans with different scanning intervals. OCTA images based on the B-scans may be combined to obtain a high dynamic range (HDR) OCTA image. Other embodiments may be described and claimed.

26 Claims, 10 Drawing Sheets
(8 of 10 Drawing Sheet(s) Filed in Color)

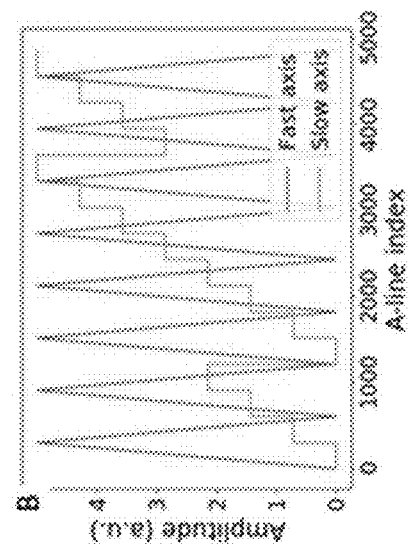
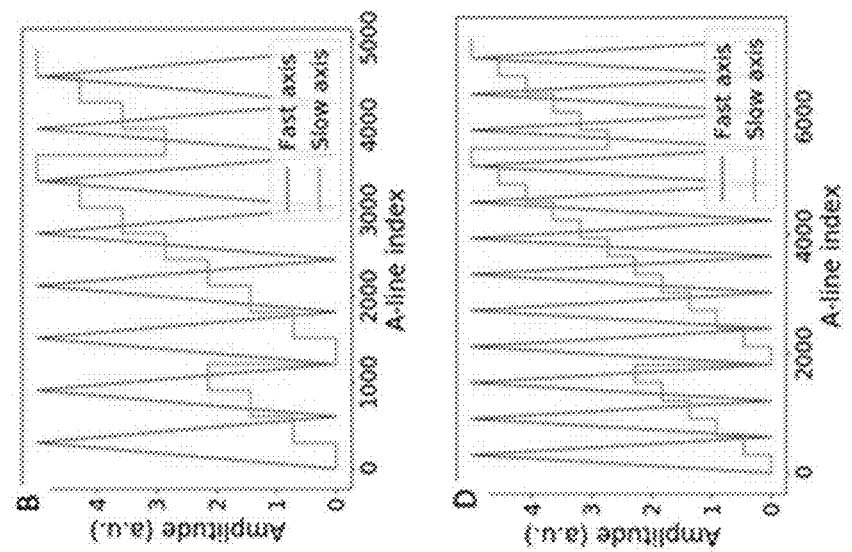
Figure 3A  Figure 3B
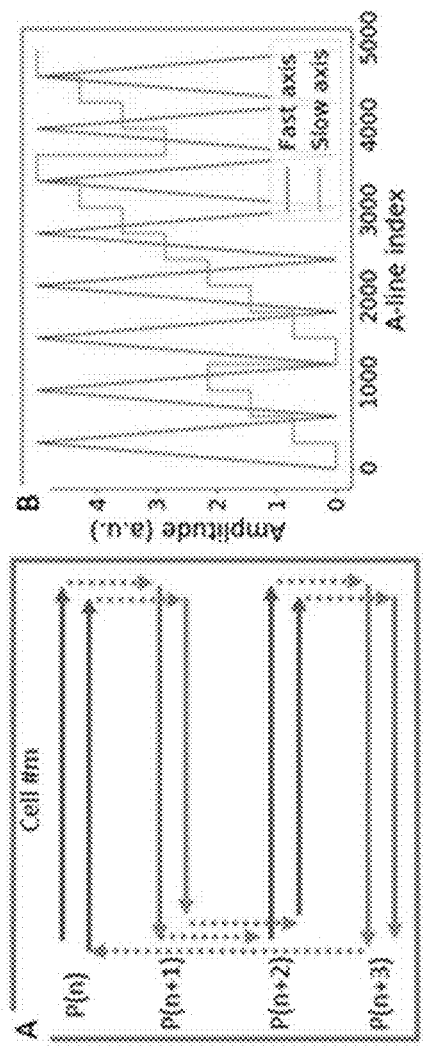
Figures 3C  Figure 3D

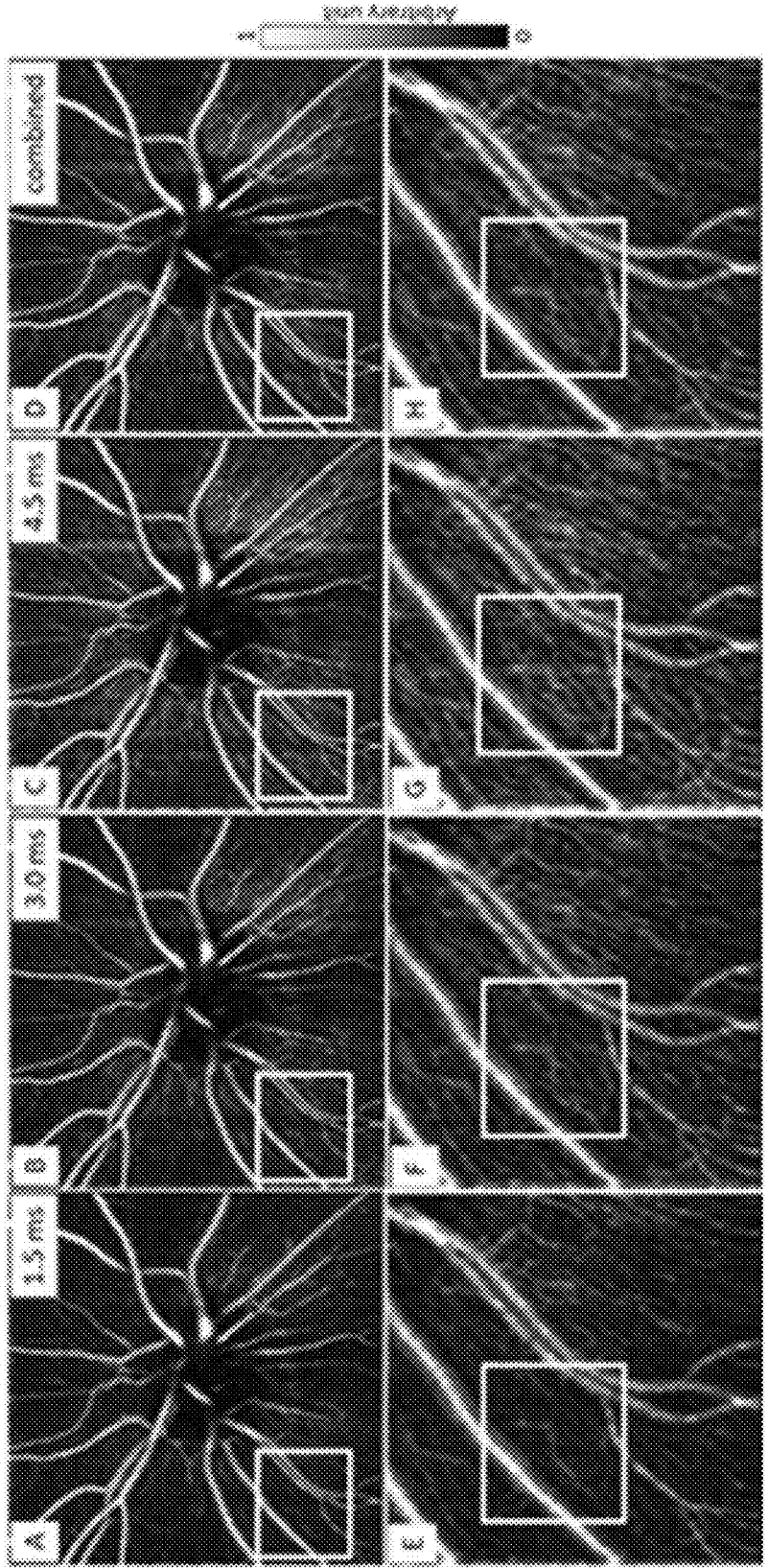

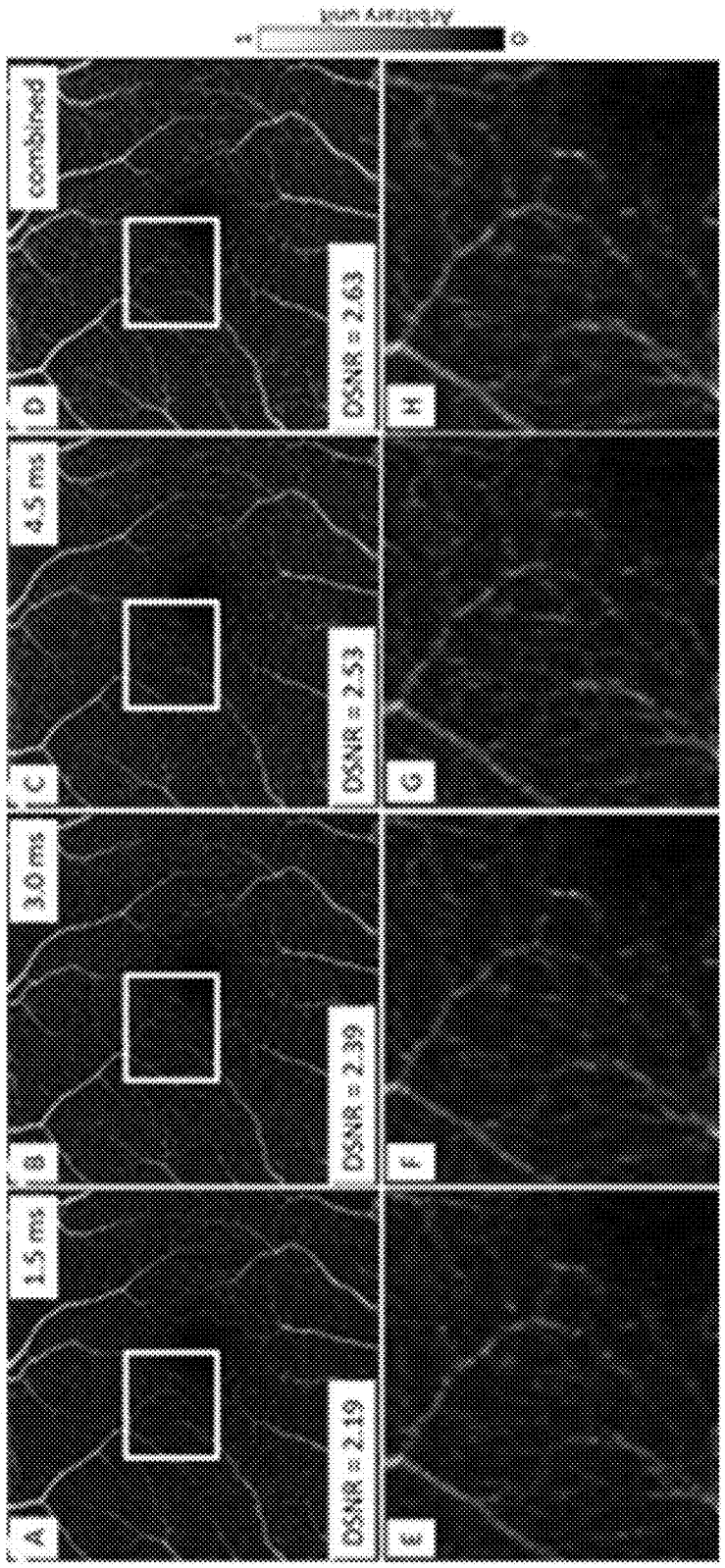

SYSTEMS AND METHODS FOR HIGH DYNAMIC RANGE OPTICAL COHERENCE TOMOGRAPHY ANGIOGRAPHY (HDR-OCTA)

CROSS REFERENCE TO RELATED APPLICATION

The present application claims priority to U.S. Provisional Patent Application No. 62/937,098, filed Nov. 18, 2019, the disclosure of which is hereby incorporated by reference.

GOVERNMENT INTEREST STATEMENT

This invention was made with government support under R01 EY027833 awarded by the National Institutes of Health. The government has certain rights in the invention.

FIELD

Generally, the field involves methods of imaging using optical coherence tomography. In particular, the field involves methods of increasing the dynamic range in optical coherence tomography angiography (OCTA).

BACKGROUND

Optical coherence tomography (OCT) angiography (OCTA) is a non-invasive modality for imaging retinal and choroidal blood flow. Compared to conventional fluorescein angiography, it does not require dye injection and so avoids deleterious, and sometimes serious, side-effects. Many OCTA algorithms have been developed; they generate depth-resolved angiograms by measuring the variation of OCT signal due to blood flow induced signal change among subsequent images. It can be computed based on the phase, amplitude, or both parts (complex OCTA) of the OCT signal. Scanning speed is a paramount performance parameter in OCT systems. The speed of commercially available OCT systems is up to 100 kHz, but experimental OCT systems have pushed into megahertz scanning rates.

Fast OCT systems have many benefits. For example, shorter scanning times reduce the incidence of motion artifacts. Fast OCT systems also enable measurements with a larger field of view (FOV), and/or make denser scanning possible, which allows high resolution in widefield OCT systems. However, higher scanning speeds may also decrease sensitivity of the OCT system and further decrease the OCTA image quality.

Laboratory and clinical studies by the present inventors have shown OCTA flow signal is affected by the time interval between consecutive B-scans. If the inter-scan time is large, the OCTA signal saturates easily for low flow velocities, and vessels carrying blood at different speeds might appear at the same signal level. In contrast, a short inter-scan time can better distinguish the different flow rate between vessels carrying fast flow; however, short inter-scan times have reduced sensitivity to slow flow, as the red blood cells do not have sufficient time to move far enough within capillaries to produce a detectable speckle variance.

Maintaining sensitivity to slow flow while increasing the flow signal dynamic range is an active topic in OCTA, and success in both aims will generate new applications relating to the detection of pathologies associated with flow rates. In photography, the dynamic range of an image can be affected by the sensitivity and noise level of the detector. Multi-exposure high dynamic range photography is an attempt to overcome this issue. It is based on the observation that the dynamic range of an image sensor is correlated to its exposure time. By combining long and short exposure images, the dynamic range of the combined image can be expanded. For OCTA, the scanning interval is analogous to the exposure time in photography. By combining short with long inter-scan times, a high dynamic range (HDR)-OCTA image can be generated.

A pilot version of HDR-OCTA, variable inter-scan time analysis (VISTA), demonstrated sufficient sensitivity to detect flow impairment before the onset of capillary dropout. However, this prior work was based on an inefficient OCT scanning protocol that had to achieve the optimal duty cycle by including an unnecessary fly-back at every B-scan across the fast scanning priority axis, and an additional superfluous cross-sectional B-scan.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 2A illustrates scanning cells that contain the lateral positions swept during OCTA data acquisition. The first scanning position of the second cell is acquired after the positions in the previous cells have been scanned two times. Orange arrows and blue arrows in FIG. 2A illustrate indicate different scanning position. FIG. 2B illustrates example details of the voltage signal applied to each galvanometer, in accordance with various embodiments.

FIGS. 3A-3D illustrate an example protocol based on combined bidirectional scanning cells, in accordance with various embodiments. FIG. 3A illustrates a basic cell containing four scanning positions. FIG. 3B illustrates a voltage signal applied on galvo mirrors for the four scanning position configuration. FIG. 3C illustrates a basic cell containing six scanning positions. FIG. 3D illustrates a voltage signal applied on galvo mirrors for the six scanning position configuration.

FIGS. 7A-7H illustrate human peripapillary retina images, in accordance with various embodiments. FIGS. 7A, 7B, and 7C illustrate three different scanning interval images with three different dynamic ranges. FIG. 7D illustrates a combined HDR-OCTA image. The white box in FIGS. 7A, 7B, 7C and 7D is expanded in respective FIGS. 7E, 7F, 7G and 7H. The region in FIGS. 7E, 7F, 7G and 7H that is highlighted using another white box shows significant difference between the different intervals.

FIGS. 8A-8H illustrate human macular retina images, in accordance with various embodiments. FIGS. 8A-8C illustrate three different scanning interval images with three different dynamic ranges. FIG. 8D illustrates a combined HDR-OCTA image. The white box in FIGS. 8A, 8B, 8C and 8D are expanded in respective FIGS. 8E, 8F, 8G and 8H.

DETAILED DESCRIPTION

Figure 1A:
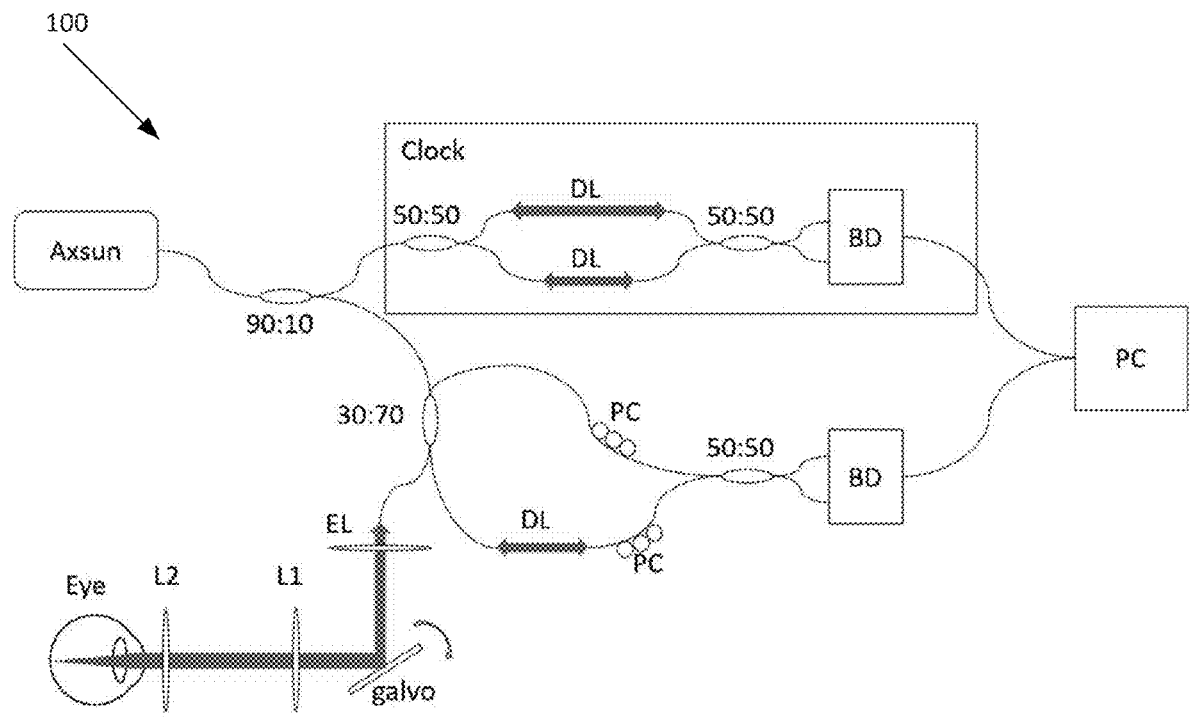
FIG. 1A schematically illustrates a system configuration an example OCT system in accordance with various embodiments. The example system shown in FIG. 1A is a 400-kHz SS-OCT system that contains two 200-kHz multiplexed swept sources. BD is a balanced detector, PC is a polarization controller, DL is a delay line, L1 is a first focus lens (e.g., 100 mm focus lens), L2 is a second focus lens (e.g., 50 mm focus lens) and EL is an electric lens.

Disclosed are methods and systems for increasing the dynamic range of optical coherence tomography (OCT) angiography (OCTA). For example, the disclosed techniques may be referred to as high dynamic range OCTA (HDR-OCTA).

Also disclosed herein is an exemplary system for acquiring OCTA images. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image. The axis orthogonal to the A-scan axis in the plane of the cross-sectional scanning location of the B-scan is referred to as the fast axis. Accordingly, the scanner travels along the fast axis while obtaining A-scans that are combined to form one B-scan. The axis orthogonal to the plane of the cross-sectional scanning location of the B-scan is referred to as the slow axis.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

The dynamic range of current optical coherence tomography (OCT) angiography (OCTA) images is limited by the fixed scanning intervals. High speed OCT devices introduce the possibility of extending the flow signal dynamic range. Embodiments in accordance with the present disclosure provide a novel scanning pattern for achieving high dynamic range (HDR)-OCTA with a superior scanning efficiency. The disclosed techniques implement a bidirectional, interleaved scanning pattern that is sensitive to different flow speeds by adjustable adjacent inter-scan time intervals. In accordance with some embodiments, an improved flow dynamic range may be achieved by generating 3 different B-scan time intervals using 3 B-scan repetitions. As used herein, the number of repetitions refers to the total number of B-scans that are obtained at the same cross-sectional scanning location (e.g., along the fast axis). Accordingly, 3 repetitions will provide 3 total B-scans at the cross-sectional scanning location.

HDR-OCTA using the bidirectional, interleaved scanning protocol described herein may achieve an optimal scanning duty cycle and obtain three different inter-B-scan intervals with only three B-scans per cross-sectional scan location as opposed to the five repetitions with only two intervals used in previous techniques.

Various aspects of the disclosed techniques are described in more detail below. For example, a system configuration for HDR-OCTA is shown and described. Additionally, in an aspect of the disclosed techniques, an HDR-OCTA image may be generated by combining multiple OCTA images with different scanning intervals. Compared to conventional OCTA technology, this method can improve more than 25% of the flow dynamic range. The HDR-OCTA image is able to show the dynamic flow change which is not visible in conventional OCTA. This technique will allow quantification of blood flow magnitude in vascular diseases.

In another aspect of the disclosed techniques, an HDR-OCTA image may be acquired by using interleaved scanning patterns. This may include a raster scan-based HDR-OCTA scan pattern and/or a bidirectional scan-based HDR-OCTA. Compared to conventional scanning patterns, this scanning pattern is more efficient. By applying interleaved raster scan-based HDR-OCTA pattern, more than 25% (save at least one repeat) of the total scanning time can be saved. Additionally, by applying interleaved bidirectional scan-based HDR-OCTA pattern, more than 45% (save at least one repeats and the fly-back time) of the total scanning time can be saved. Because of the high efficiency, this technology can be applied to current commercially available OCT systems without updating the scanning speed. It can also further expand the dynamic range in a future high-speed OCT system.

Figure 11:
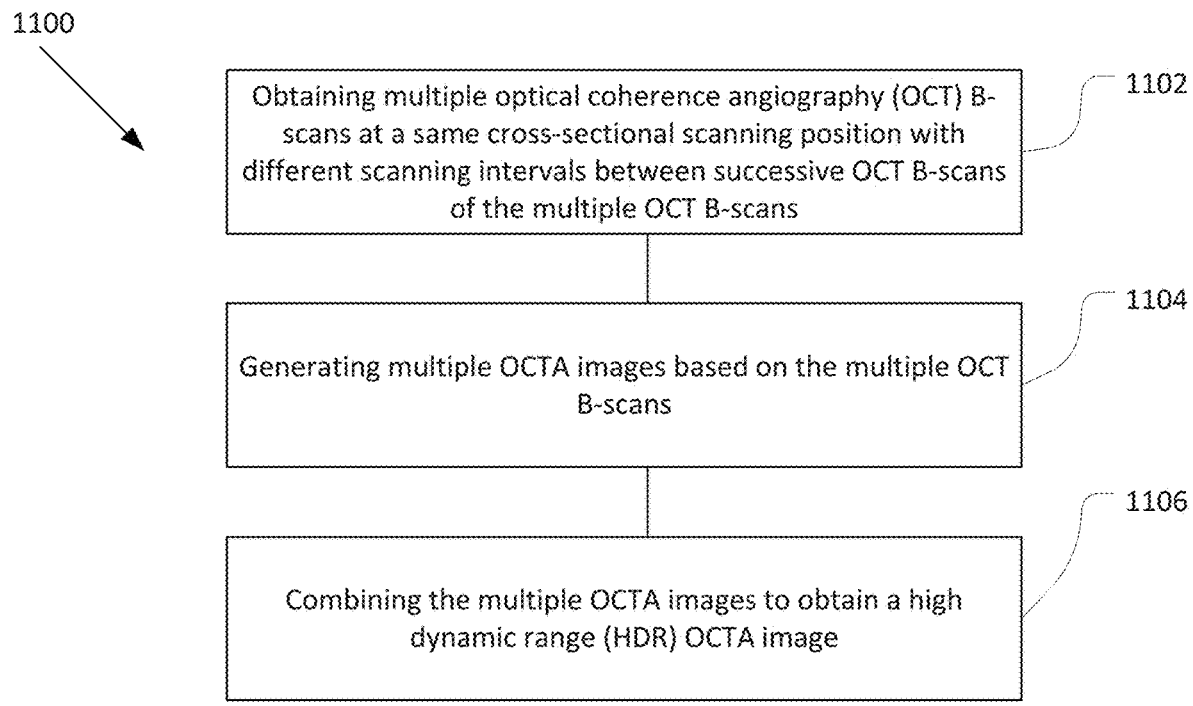
FIG. 11 is a flowchart of an example method for HDR-OCTA, in accordance with various embodiments.

This disclosure provides both a system and method for HDR-OCTA. For example, FIG. 11 illustrates a method 1100 for HDR-OCTA in accordance with some embodiments.

At 1102, the method 1100 may include obtaining multiple optical coherence angiography (OCT) B-scans at a same cross-sectional scanning position with different scanning intervals between successive OCT B-scans of the multiple OCT B-scans. In some embodiments, additional B-scans at one or more other cross-sectional scanning positions may be obtained between the B-scans at the same cross-sectional position (e.g., using an interleaved scanning pattern), as further described herein. Additionally, or alternatively, some embodiments may use a bidirectional scanning pattern to obtain B-scans of the sample. In other embodiments, a raster-based scanning pattern may be used.

At 1104, the method 1100 may include generating multiple OCTA images based on the multiple OCT B-scans. The OCTA images may be generated, for example, by determining flow values using respective pairs of the OCT B-scans. The flow values may be decorrelation values or other suitable values that are indicative of flow in the sample. For example, using three B-scans at the same cross-sectional position, three OCTA images may be generated using three different pairs of the B-scans (e.g., scan 1 and scan 2, scan 2 and scan 3, and scan 1 and scan 3). Accordingly, the different OCTA images will each be based on different scanning intervals between the associated OCT B-scans.

At 1106, the method 1100 may include combining the multiple OCTA images to obtain a high dynamic range (HDR) OCTA image. For example, the combined image may be generated by adding the multiple (e.g., three) OCTA images together (e.g., adding the respective values of each voxel in the OCTA images).

Further detail and/or example implementations of various aspects of the method 1100 are described below.

Amplitude-Based OCTA Signal Processing

Split-spectrum amplitude-decorrelation angiography (SSADA) is a commercialized OCTA algorithm that offers superior angiogram image contrast and quality. The flow signal in SSADA is extracted using the decorrelation value from each of several spectrums split from the entirety of the signal generated by repeated B-scans. The application of the split-spectrum approach improves the signal to noise ratio of OCTA images and the flow tissue contrast. The fundamental theory of SSADA may be expressed as:

$$\overline{D}_{SSADA}(x, z) = \\ 1 - \frac{1}{N-1} \cdot \frac{1}{M} \sum_{n=1}^{N-1} \sum_{m=1}^{M} \frac{A_{n,m}(x,z) \cdot A_{n+1,m}(x,z)}{\frac{1}{2}A_{n,m}(x,z)^2 + \frac{1}{2}A_{n+1,m}(x,z)^2}. \quad (1)$$

Here, the decorrelation signal $\overline{D}_{SSADA}$ is calculated as an average over the N repeats for each scanning location and the M divisions of the full spectrum. For each split-spectrum at each repeat, the autocorrelation with the subsequent scan is calculated using OCT intensity signals $A_n(x,z) \cdot A_{n+1}(x,z)$. The autocorrelation of the laser speckle signal $g(\tau)$ may be represented as:

$$g(\tau) = I^2 \cdot \exp\left(-\frac{|\tau|}{\tau_c}\right). \quad (2)$$

Here, $\tau$ is the exposure time and $l$ is the amplitude of the speckle signal, which in OCTA can be correlated to the scanning interval. $\tau_c$ is the correlation coefficient, which can be related to the flow speed $v_{flow}$, bulk motion $v_{bulk}$ and Brownian motion $v_{brownian}$, according to:

$$\tau_c \cdot (v_{flow} + v_{brownian} + v_{bulk}) = k, \quad (3)$$

where it may be assumed that $\tau_c$ obeys a linear relationship with the motion. Thus, $$g_g(\tau) = I^2 \exp\left(-\frac{\tau \cdot (v_{flow} + v_{brownian} + v_{bulk})}{k}\right). \quad (4)$$

The value k is a constant. Here, $\tau$ represents the scanning interval, which is equivalent to the exposure time in Eq. (2). Eq. (1) may then be written as:

$$\overline{D}_{SSADA} = 1 - \exp\left(-\frac{\tau \cdot (v_{flow} + v_{brownian} + v_{bulk})}{k}\right). \quad (5)$$

Accordingly, the relationship between the SSADA signal and the flow is an exponential relationship. The sensitivity of $v_{flow}$ is related to the scanning interval $\tau$, and also the dynamic range or the linearity of $\overline{D}_{SSADA}$ is determined by $\tau$.

Conventional OCTA systems use a raster scanning pattern in which the scanning interval between each repeat is fixed and cannot be changed during data acquisition. This usually results in a narrow flow signal dynamic range. Therefore, conventional OCTA doesn't carry much flow rate information and is frequently used just to measure the location of vasculature. To generate HDR-OCTA images reflecting blood flow rate, a high-speed OCT system and a novel multi-interval scanning method is described herein.

400 k Swept Source (SS)-OCT System

Figure 1B:
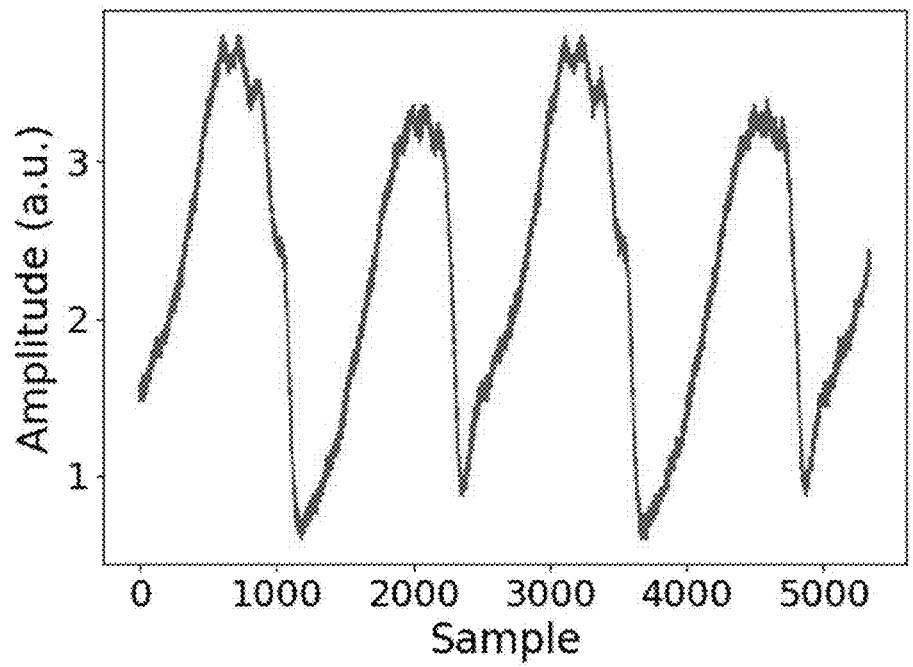
FIG. 1B graphically illustrates spectrum of the 400-kHz AXSUN laser that may be used in the OCT system of FIG. 1A, where S1 and S2 are the spectra of the individual 200-kHz swept sources.

FIG. 1A illustrates an example SS-OCT system 100, in accordance with various embodiments. The SS-OCT system 100 includes a 400-kHz swept source laser (AXSUN Technologies) with center wavelength of 1060 nm and 100 nm bandwidth. Two 200-kHz swept laser engines with 50% duty cycles may be combined to achieve a total swept rate of 400-kHz with 100% duty cycle (see FIG. 1B). The laser engine does not contain a built-in k-space clock (k-clock) signal output, so a Mach-Zehnder interferometer may be built using 10% of the output power from the laser to provide the high-speed k-clock, linearly sampling the spectrum in k-space. An optic coupler (e.g., 70:30 optic coupler) may be used to split the power to the reference and sample arm. The optical power on the pupil can be controlled with a variable attenuator (e.g., set to 2 mW). The data may be acquired using a 1.8 GS/s ATS9360 (Alazar, Inc.) digitizer and 1 GHz balanced detectors (Thorlabs, Inc.). A 3-mm galvo scanner (ScannerMax) may be used to scan the laser beam. The axial resolution of 5.5 μm and the imaging depth of 4.2 mm in the air may be achieved by sampling across the total 100 nm bandwidth with 1536 sampling points. The beam size on the pupil may be 1.2 mm and the lateral resolution may be 19 μm. The power and spectrum shape of the two lasers are slightly different (see FIG. 1B); during data processing, data acquired from each laser may be processed separately. The sensitivity of this system was measured to be 120 dB. The SS-OCT system 100 may also include a real-time GPU-based OCT display and data acquisition software.

It will be apparent that the SS-OCT system 100 described herein and depicted in FIG. 1A is merely an example, and modifications to the SS-OCT system 100 may be made within the scope of the present disclosure.

Bidirectional Scanning Protocols Opts Out of Fly-Back Time

OCT scanning of the retina is commonly performed using a raster scan pattern by applying a sawtooth voltage function on the galvanometer mirror for the fast-axis and a step function for the slow-axis. The most commonly used scanner is based on two galvo motors precisely driving reflection mirrors. The galvo motors have a response time which is limiting the maximum resonant frequency. Therefore, in single sided scanning pattern, several hundred micro-seconds of fly-back time is required to reset the scanner to the original position before the scan steps into next position. For a high-speed OCT system (200 kHz), the fly-back can be, for example, half of the total scanning time depending on the scanning size and density. In such cases the effective duty cycle is only 50%, so half of the total scan time is wasted.

Figures 2A, 2B:
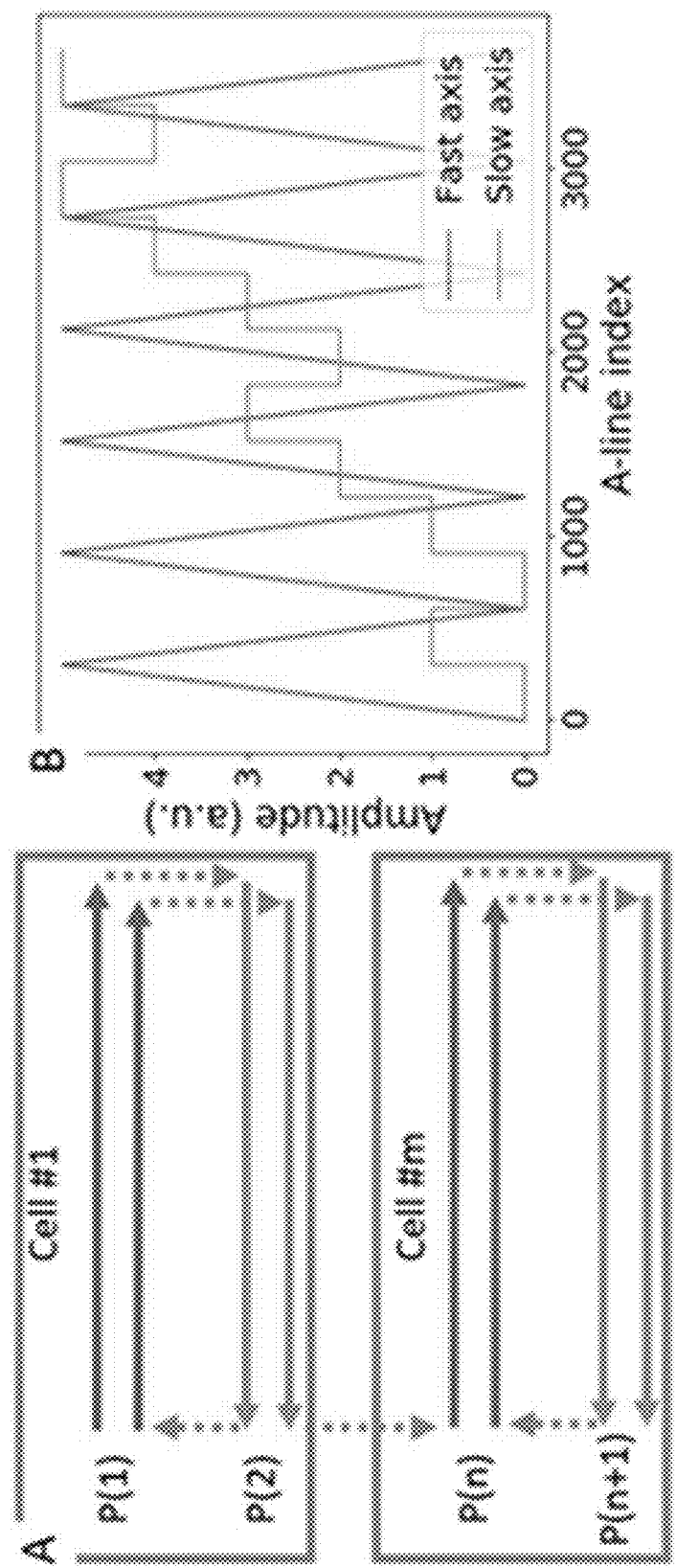
FIGS. 2A and 2B illustrate an example of one bidirectional scanning protocol, in accordance with various embodiments.

Some prior scanning patterns have been developed to eliminate fly-back and increase scanning speed and efficiency. Examples include Lissajous scanning, constant linear velocity spiral scanning, and constant angular velocity spiral scanning. However, these methods all require an additional step to resample the image into Cartesian coordinates, which increases the complexity of image post-processing. A bidirectional scanning protocol (e.g., as shown in FIG. 2) using a triangular function on the fast-axis may be used (e.g., on a 200-kHz SS-OCT system). The forward scanning and the backward scanning are consecutively acquired without the use of fly-back scans. By applying this scheme, the scan duty cycle is increased to almost 100%.

Bidirectional Scanning Protocols Sustain Reasonable Time Delay and Efficiency for High-Speed OCTA Considering that the optimal time delay between B-scans is around 3-5 milliseconds (ms) for OCTA of capillary blood flow, in higher speed OCT systems using conventional raster scans the number of A-lines acquired in each B-scan has to be very large to ensure a reasonable scan interval. Although this results in a higher A-line density sampling, it does not necessarily translate into better lateral resolution, which is fundamentally limited by numerical aperture of the eye and ocular aberrations. Moreover, high speed systems also demand that the raster scanning pattern dedicate the same amount of time and therefore more A-lines per B-scan to the fly-back portion in order to avoid mechanical damage on the scanning hardware. For these reasons the conventional raster scanning pattern is an inefficient option. Conversely, a bidirectional scan pattern can be adapted to provide reasonable B-scan time delays by increasing the number of positions along slow-axis positions acquired within one unit (see FIGS. 3A-3D). For example, the B-scan interval can be doubled by combining four positions into one scanning unit (see FIGS. 3A and 3B); and tripled by combining six positions into one scanning unit (see FIGS. 3C and 3D), e.g., depending on the needs imposed by the A-line rates of the system.

Bidirectional, Interleaved Scanning Patterns Achieve HDR-OCTA

As discussed above, the flow dynamic range depends on the B-scan time interval. Conventional, equal interval scanning patterns have only one single, fixed scanning interval between two scan repetitions at a location. If multiple scanning intervals are desired, the number of repetitions should be carefully considered, since the number of repeated scans also determines the total time for completing a single scan volume. For a fixed scan interval, the number of repetitions at a location must exceed the number of different scanning intervals, since a scan interval will always be encapsulated by two scans. However, by carefully choosing different scan interval lengths, this limit can be bypassed. For variable length scan intervals, the total number of scan intervals N interval that are constructed from $N_{B\text{-}scan}$ of B-scans can be calculated from the binomial coefficient as:

$$N_{interval} = \binom{2}{N_{B\text{-}scan}}. \tag{6}$$

Figures 4A, 4B:
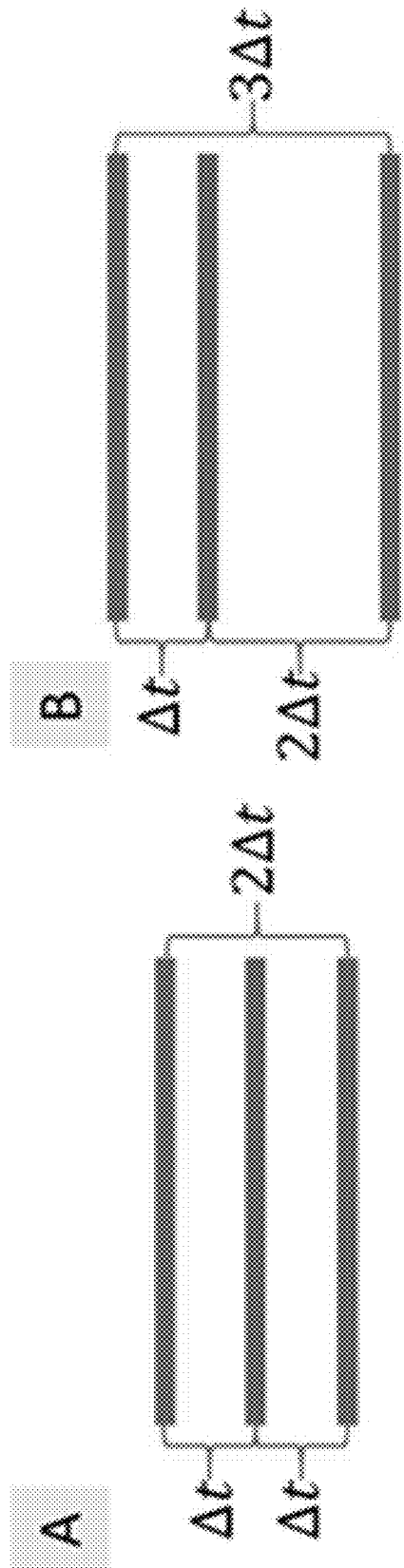
FIG. 4A illustrates an equal interval scanning method, for which the total number of intervals available for measurements is two, corresponding to $\Delta t$ and $2\Delta t$.
FIG. 4B illustrates an interleaved scanning method, which achieves the number of scan intervals from the same number of scans, as given by Eq. (6) discussed further below. In this case, 3 different scanning intervals ($\Delta t$, $2\Delta t$, and $3\Delta t$) are obtained from 3 B-scans.

The total number of scan intervals, N interval, is not just the number of different intervals between adjacent scans, since non-adjacent repetitions can also be used to construct a different scan interval. So, for example, if there are three repetitions, the total number of different scanning intervals that can be constructed from equal interval scans is two (see FIG. 4A). However, if the second scanning interval is twice the duration of the first scanning interval, then there are 3 total scan intervals (see FIG. 4B).

Figure 5B:
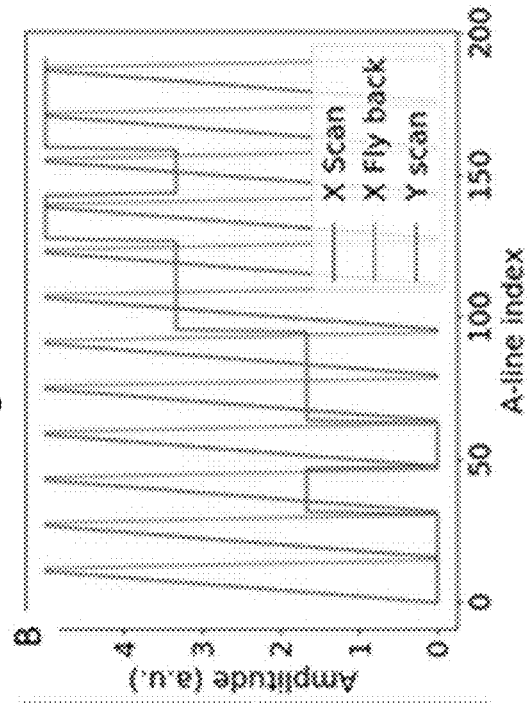
FIG. 5B illustrates a signal applied to the galvo scanner.
Figure 5D:
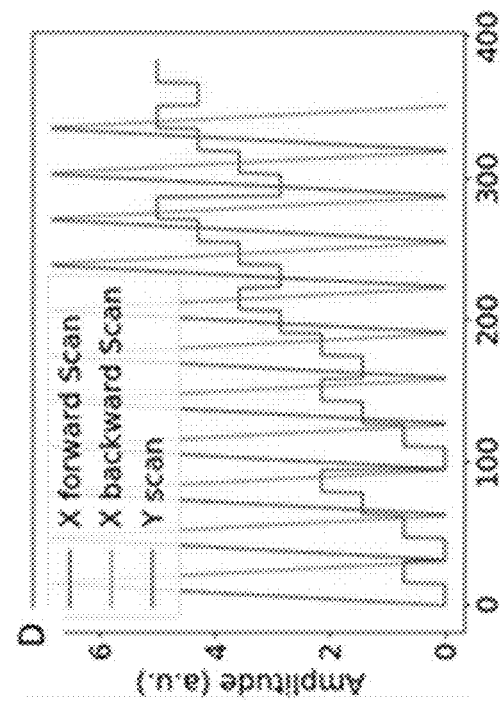
FIG. 5D illustrates a signal applied to the galvo scanner for the HDR-OCTA scan pattern. X axis is the fast axis, Y axis is the slow axis.
Figure 5A:
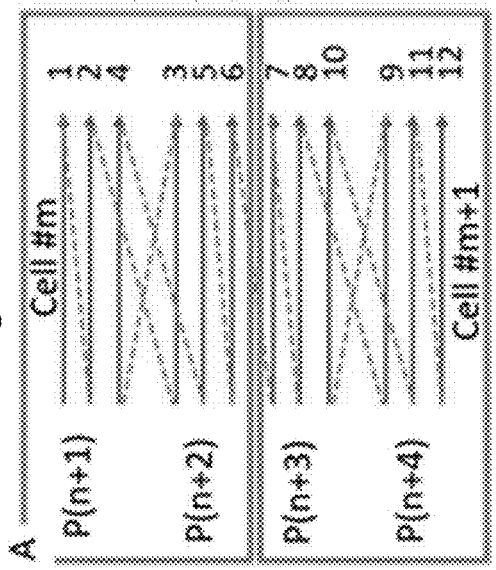
FIG. 5A is a diagram to show the raster scan based HDR-OCTA scan pattern. Orange lines indicate flyback movements.
Figure 5C:
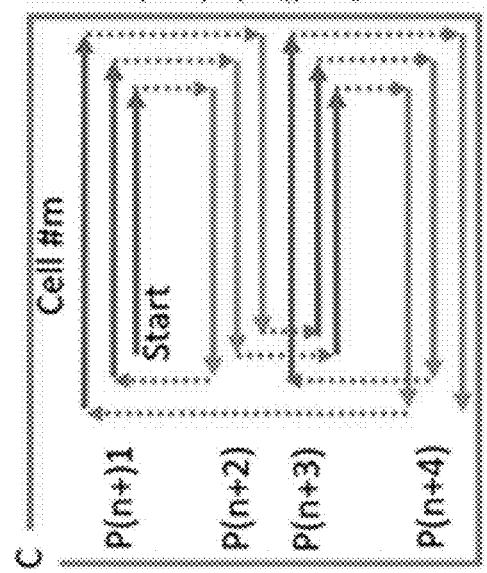
FIG. 5C illustrates a bidirectional HDR-OCTA scanning pattern.

To achieve this, a special scanning sequence is needed. An interleaved raster scanning pattern may be designed first to modify the second scanning interval. In this scanning pattern, every two cross-sectional positions form a scanning unit, and the scanning pattern in each unit is the same. The scanner first scans one position twice and then scans the next position once and returns back to scan the original position a third time (see FIGS. 5A and 5B). By doing so, the second scanning interval from the three repetitions will be twice the duration of the first scanning interval. However, the raster scanning pattern includes non-efficient fly-backs, which are especially problematic on a high-speed system due to limits in galvo motor speed. To overcome this problem, a bidirectional HDR-OCTA scanning pattern may be used as described herein (see FIGS. 5C and 5D).

In various embodiments of the scanning protocol, the time between the first and second repetition is different than the time between second and third repetition, allowing a total of 3 different inter-scan times (1-2, 2-3 and 1-3). The larger number of interscan times improves the dynamic range of the system and the in vivo HDR scan can be acquired in less than two seconds. This minimizes the prevalence of motion artifacts, which are more predominant in the scanning intervals most sensitive to slow speed flow.

Flow Phantom Experiment

As indicated in Eq. (5), the flow and OCTA signal have an exponential relationship. The in vivo OCTA dynamic range can be expanded by applying different scanning intervals, however it is difficult to quantify dynamic range in vivo. In various embodiments, a flow phantom experiment may be used to study the dynamic range change resulting from different scanning intervals and patterns quantitatively. The flow phantom experiment may use a flow phantom connected to a syringe pump that can be set to different flow rates. For example, a 250 μm inner diameter glass tubing may be used. The tubing may be placed on a paper board and then sealed using hot melt glue. Hot melt glue, as a semi-transparent material, can be treated as background tissue. In one experiment, the blood sample used in the tubing was bovine blood (Carolina Biological Supply Company). The flow speed was manually set from 0 to 6 millimeters per second (mm/s), with steps of 0.3 mm/s. The whole experiment setup and the OCT system sample arm were placed on an air insulated optical table to prevent the vibrations.

Experimental Results

Dynamic Range can be Expanded Using HDR-OCTA

Figures 6A, 6B:
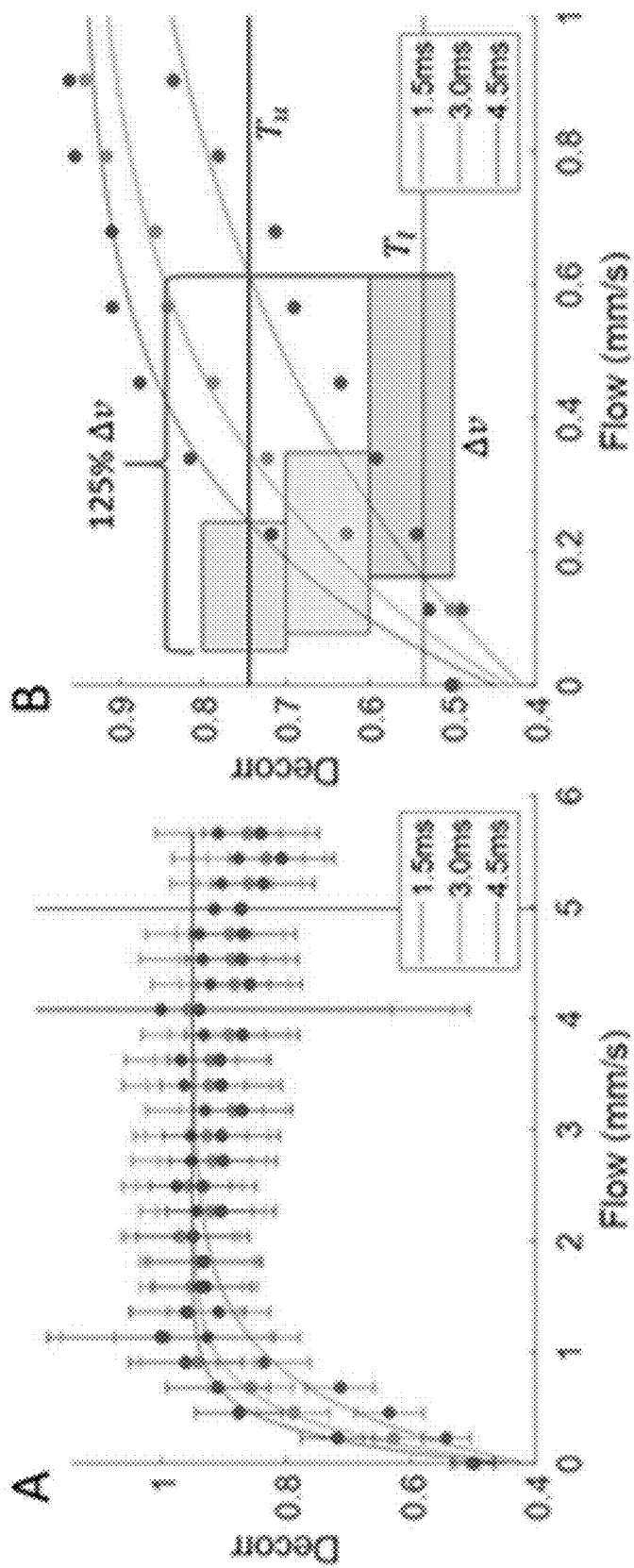
FIG. 6A illustrates fitted flow phantom experiment results at different scanning intervals and flow speeds, in accordance with various embodiments.
FIG. 6B illustrates dynamic range calculated using experimental data. The shaded rectangular boxes indicate the dynamic range of different scanning intervals. Δv: dynamic range of 1.5 interval, dynamic range after combining three intervals is increased by 125%. $T_u$: upper threshold, $T_l$: lower threshold.

A flow phantom cross-sectional image was acquired in a single location. 128 B-scans were acquired. In the acquired data set, the scanning intervals between adjacent B-scans were 1.5 ms; the interval between every two B-scan were 3 ms, and the interval between every three B-scan was 4.5 ms. From this data set it is possible to construct a total of 125 OCTA B-scans at the longest time (since the last 3 scans lack additional scans that could be used to obtain a 4.5 ms interval). Using this data set, the flow value D was calculated by averaging over the tubing area in each OCTA B-scan. Each data set contains 125 decorrelations. From these, the mean decorrelation value $\overline{D}$ was calculated. FIG. 6A illustrates a plot of $\overline{D}$ corresponding to different flow speeds and fit using Eq. (5). The data follows the theoretical prediction (see FIG. 6A). Additionally, thresholds were defined for the dynamic range of the system according to these measurements. The lower threshold for each scanning interval is defined using the minimum of the decorrelation value $D_{min}$ plus the standard deviation of the decorrelation values $D_{std}$ of each data set (Eq. 7).

$$D_{std} = \text{std}(D) \tag{7}$$

The upper threshold decorrelation value is defined analogously, but by subtracting $D_{std}$ from the averaged saturated decorrelation values, $D_{max}$. That is, an upper threshold $T_u$ (Eq. 8) and a lower threshold $T_l$ (Eq. 9) may be defined as follows:

$$T_u = D_{max} - D_{std} \tag{8}$$

$$T_l = D_{min} + D_{std} \tag{9}$$

The upper threshold and the lower threshold were overlapped across three different scanning intervals. The overlapping threshold is expected, which is only dependent on the sensitivity of the detector. According to this flow phantom experiment, the dynamic range is improved by 25% by applying the multi-scanning interval (see FIG. 6B).

In Vivo Retinal Imaging

Five healthy human retinal images were acquired using a 400-kHz swept-source OCT system by an experienced OCT operator. The data sets have 304 A-line per B-scan and 912 B-scans with 3 repeats per volume. The scanning size is 3×3 $mm^2$. In the slow axis direction, the data was over sampled to improve the signal to noise ratio. Both macular and optic nerve head regions were acquired. Three different scanning intervals 1.5 ms, 3 ms and 4.5 ms were generated in single data set. The data was processed using the SSADA algorithm with eleven split spectra. The images were then segmented into seven layers using automatic segmentation software. The inner retina en face projection images were generated using the maximum projection from the internal limiting membrane (ILM) to the outer plexiform layer (OPL). The en face images were normalized according to the maximum and minimum values. A custom angiogram colormap was applied to the images to improve the vessel contrast. The combined images were generated after application of a fixed threshold to each en face image from different scanning intervals. In the peripapillary retinal angiograms, the 1.5 ms and 3 ms images show less capillary structure than the 4.5 ms image, but the 4.5 ms image has more noise than the 1.5 ms and 3 ms images. The combined image is generated by adding three images together. The combined HRD OCTA image demonstrates the best capillary visibility and has the least noise (see FIGS. 7A-7H).

In the macular retina, there is less variation in blood flow velocity, and it is difficult to distinguish the change between different scanning intervals. Here, the decorrelation signal to noise ratio (DSNR) of each individual image was calculated. The DSNR is increasing as the scanning interval becomes longer. The combined image has the largest DSNR. Additionally, in the macular angiograms (see FIGS. 8A-8H), the 1.5 ms image has less capillary structure than the 4.5 ms image, and the 4.5 ms image has more noise than the 1.5 ms image. The combined image shows more details from the capillaries and at the same time has a lower noise level.

DISCUSSION

As discussed herein, various embodiments provide a superior scanning pattern for high speed OCTA data acquisition that increases the dynamic range of flow measurements in the most efficient way, thereby achieving this with the minimum total scan duration. In the in vitro study there was an increase of 25% in the dynamic range of flow measurements compared to a conventional raster scan pattern, and in vivo measurements indicate that the disclosed method successfully removes noise and can potentially allow additional quantification of flow magnitude in retinal images.

The ability to better quantify flow magnitude in particular represents a major aspiration for OCTA technology. Currently, commercial instruments and most OCTA studies are limited in scope to simply quantify vascular patterns and organization, without the ability to quantify blood flow magnitude. There are indications in both diabetic retinopathy (DR) and age-related macular degeneration (AMD) that flow impairment occurs during disease progression, and previous work has established flow impairment adjacent to regions of geographic atrophy. There is, then, reason to believe that flow magnitude is clinically significant. Without a reliable method to measure flow speed frequently and rigorously in vivo, it is unknown to what extent changes in flow may be indicative of disease progression. It is possible that we may gain access to a host of biomarkers and indicators for treatments if given the ability to measure flow magnitude, even if they are still limited relative flow measurements. Future studies that could explore the link between flow magnitude and pathology must wait for instruments with high dynamic ranges; the HDR-OCTA systems and methods described herein represent an important step in that direction. And, without regard to pathology, there are also basic research questions that measurements of flow magnitude can address.

The HDR-OCTA techniques described herein provide the optimal scan pattern for three B-scan repeats. The efficiency of this scan pattern is significant because it enables growth of the dynamic range of OCTA scans without sacrificing total scan duration. Compared to previous works, the method described herein is capable of capturing the same dynamic range with less total scanning time. This is going to become more important as the speed of commercial and experimental systems continues to grow, both because the returns on scan efficiency will be greater, and because the potential increase in dynamic range will be larger.

Some embodiments are described with respect to an optimal scanning pattern for 3 B-scans at a single location. The interleaved scanning pattern allows measurement of flow from three different scanning intervals using this approach, but the experimental results indicated that this number of scan repetitions is limited to an increase of 25% in flow signal dynamic range. To further extend the dynamic range further, it will require more scan repetitions at a single location; however, with faster OCT systems more repetitions become more plausible. The trade-off between scan volume acquisition time and dynamic range as parametrized by number of repeats may be weighed. Defining the contours of this relationship may allow the clinical community to decide on the number of repetitions based on the needs of personalized care for specific diseases. In addition, it will be useful to extend HDR-OCTA into wide field imaging regimes. The variation in flow speed is more pronounced between different regions of the retina, so the benefit of measuring this variation will be more pronounced in wide field systems. As OCT technology as a whole moves in this direction, HDR-OCTA represents a promising, complimentary addition to other extensions of the technology.

Accordingly, as demonstrated above, high-speed OCTA has enabled the observation of blood flow change. The dynamic range of OCTA is a key factor that limits the contrast to flow change. The present disclosure described a bidirectional scanning pattern and compared it with the conventional raster scan pattern. A novel interleaved scanning pattern is described herein for both raster and bidirectional scanning methods. The results from a flow phantom experiment quantitatively verified the possibility of expanding the dynamic range through a multi-interval scanning method. In vivo human peripapillary and macular images were also successfully acquired using the bidirectional interleaved scan pattern. The improvement of dynamic range was verified by comparing OCTA images with three different intervals and the final combined image (HDR-OCTA).

Example Optical Coherence Tomography
Angiography Image Processing System

Figure 9:
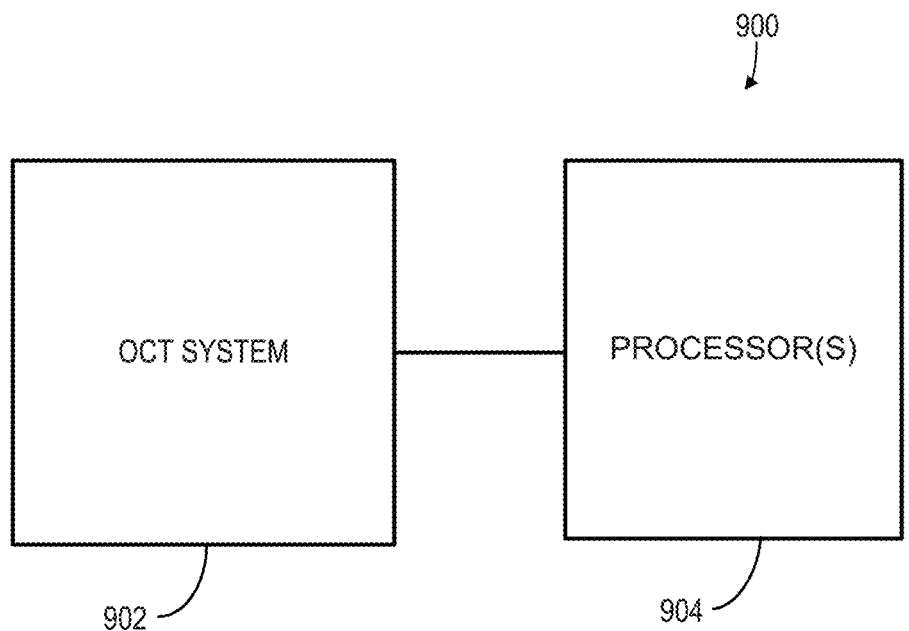
FIG. 9 schematically shows an example system for retinal capillary oximetry using OCT, in accordance with various embodiments.

FIG. 9 schematically shows an example system 900 for OCT image processing in accordance with various embodiments. System 900 comprises an OCT system 902 configured to acquire an OCT image comprising OCT interferograms and one or more processors or computing systems 904 that are configured to implement the various processing routines described herein. OCT system 900 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods and processes for HDR-OCTA described above, can be implemented as a computer application, computer service, computer API, computer library, and/or other computer program product.

Figure 10:
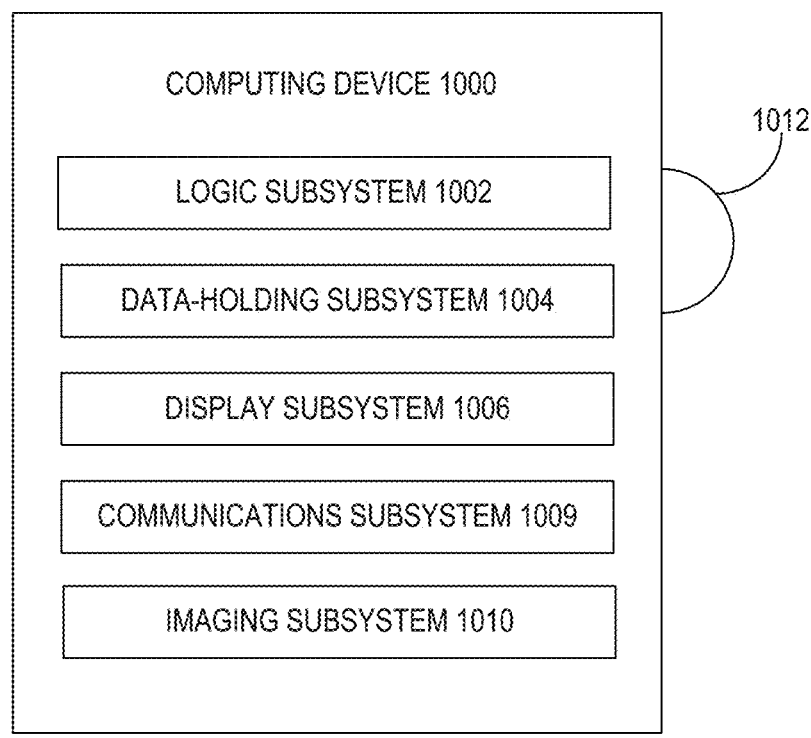
FIG. 10 schematically shows an example of a computing system in accordance with the disclosure.

FIG. 10 schematically shows a non-limiting computing device 1000 that can perform one or more of the above described methods and processes. For example, computing device 1000 can represent a processor included in system 900 described above, and can be operatively coupled to, in communication with, or included in an OCT system or OCT image acquisition apparatus. Computing device 1000 is shown in simplified form. It is to be understood that virtually any computer architecture can be used without departing from the scope of this disclosure. In different embodiments, computing device 1000 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1000 includes a logic subsystem 1002 and a data-holding subsystem 1004. Computing device 1000 can optionally include a display subsystem 1006, a communication subsystem 1008, an imaging subsystem 1010, and/or other components not shown in FIG. 10. Computing device 1000 can also optionally include user input devices such as manually actuated buttons, switches, keyboards, mice, game controllers, cameras, microphones, and/or touch screens, for example.

Logic subsystem 1002 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1004 can include one or more physical, non-transitory, devices configured to hold data and/or instructions executable by the logic subsystem to implement the herein described methods and processes. When such methods and processes are implemented, the state of data-holding subsystem 1004 can be transformed (e.g., to hold different data).

Data-holding subsystem 1004 can include removable media and/or built-in devices. Data-holding subsystem 1004 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1004 can include devices with one or more of the following characteristics: volatile, nonvolatile, dynamic, static, read/write, read-only, random access, sequential access, location addressable, file addressable, and content addressable. In some embodiments, logic subsystem 1002 and data-holding subsystem 1004 can be integrated into one or more common devices, such as an application specific integrated circuit or a system on a chip.

FIG. 10 also shows an aspect of the data-holding subsystem in the form of removable computer-readable storage media 1012, which can be used to store and/or transfer data and/or instructions executable to implement the herein described methods and processes. Removable computer-readable storage media 1012 can take the form of CDs, DVDs, HD-DVDs, Blu-Ray Discs, EEPROMs, flash memory cards, USB storage devices, and/or floppy disks, among others.

When included, display subsystem 1006 can be used to present a visual representation of data held by data-holding subsystem 1004. As the herein described methods and processes change the data held by the data-holding subsystem, and thus transform the state of the data-holding subsystem, the state of display subsystem 1006 can likewise be transformed to visually represent changes in the underlying data. Display subsystem 1006 can include one or more display devices utilizing virtually any type of technology. Such display devices can be combined with logic subsystem 1002 and/or data-holding subsystem 1004 in a shared enclosure, or such display devices can be peripheral display devices.

When included, communication subsystem 1008 can be configured to communicatively couple computing device 1000 with one or more other computing devices. Communication subsystem 1008 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1000 to send and/or receive messages to and/or from other devices via a network such as the Internet.

When included, imaging subsystem 1010 can be used acquire and/or process any suitable image data from various sensors or imaging devices in communication with computing device 1000. For example, imaging subsystem 1010 can be configured to acquire OCT image data, e.g., interferograms, as part of an OCT system, e.g., OCT system 902 described above. Imaging subsystem 1010 can be combined with logic subsystem 1002 and/or data-holding subsystem 1004 in a shared enclosure, or such imaging subsystems can comprise periphery imaging devices. Data received from the imaging subsystem can be held by data-holding subsystem 1004 and/or removable computer-readable storage media 1012, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for optical coherence tomography angiography (OCTA) imaging, comprising:
   obtaining three or more optical coherence tomography (OCT) B-scans at each of a plurality of cross-sectional positions along a slow axis using a stepped scanning pattern on the slow axis, wherein the obtaining the OCT B-scans includes:
   obtaining a first OCT B-scan, a second OCT B-scan, and a third OCT B-scan at a first cross-sectional position of the cross-sectional positions, wherein a first time period between the first and second OCT B-scans is different than a second time period between the second and third OCT B-scans, and wherein a third time period between the first and third OCT B-scans is different than the first and second time periods; and
   obtaining, via the stepped scanning pattern on the slow axis, at least one of the OCT B-scans at one or more other cross-sectional positions of the plurality of cross-sectional positions in between the first and second OCT B-scans or second and third OCT B-scans at the first cross-sectional position;
   generating multiple OCTA images based on the three or more OCT B-scans at each of the plurality of cross-sectional positions; and
   combining the multiple OCTA images to obtain a high dynamic range (HDR) OCTA image.

2. The method of claim 1, wherein the obtaining the OCT B-scans includes:
   obtaining the first OCT B-scan at the first cross-sectional position;
   obtaining a first number of the OCT B-scans at the one or more other cross-sectional positions after obtaining the first OCT B-scan;
   obtaining the second OCT B-scan at the first cross-sectional position after obtaining the first number of OCT B-scans;
   obtaining a second number of OCT B-scans at one or more additional cross-sectional positions, of the plurality of cross-sectional positions, after obtaining the second OCT B-scan, wherein the second number is different than the first number; and
   obtaining the third OCT B-scan at the first cross-sectional position after obtaining the second number of OCT B-scans.

3. The method of claim 2, wherein the first number of OCT B-scans is one, and wherein the second number of OCT B-scans is greater than one.

4. The method of claim 3, wherein the second number of OCT B-scans is 3.

5. The method of claim 2, wherein the OCT B-scans are obtained using bidirectional scanning.

6. The method of claim 1, wherein the obtaining the OCT B-scans includes:
   obtaining the first OCT B-scan at the first cross-sectional position;
   obtaining the second OCT B-scan at the first cross-sectional position after obtaining the first OCT B-scan;
   obtaining the one or more OCT B-scans at the one or more other cross-sectional positions after obtaining the first and second OCT B-scans; and
   obtaining the third OCT B-scan at the first cross-sectional position after obtaining the one or more OCT B-scans at the one or more other cross-sectional positions.

7. The method of claim 6, wherein the first and second OCT B-scans are obtained sequentially.

8. The method of claim 7, further comprising performing a flyback of a scanner between obtaining the first and second OCT B-scans.

9. The method of claim 6, wherein the obtaining one or more OCT B-scans at the one or more other cross-sectional positions comprises obtaining one OCT B-scan at a second cross-sectional position that is adjacent to the first cross-sectional position along the slow axis.

10. The method of claim 6, wherein the OCT B-scans are obtained using raster scanning.

11. The method of claim 6, wherein the one or more OCT B-scans at the one or more other cross-sectional positions are a first number of OCT B-scans, and wherein the method further comprises obtaining a second number of the OCT B-scans at one or more additional cross-sectional positions, of the plurality of cross-sectional positions, between obtaining the first OCT B-scan and obtaining the second OCT B-scan.

12. The method of claim 1, wherein the OCT B-scans are obtained via bi-directional scanning, wherein the at least one of the OCT B-scans at one or more other cross-sectional positions includes a first OCT B-scan and a second OCT B-scan at a second cross-sectional position, and wherein the obtaining the OCT B-scans includes:
   sequentially obtaining the first OCT B-scan at the first cross-sectional position and the first OCT B-scan at the second cross-sectional position;

sequentially obtaining, after obtaining the first OCT B-scans at the first and second cross-sectional positions, the second OCT B-scan at the first cross-sectional position and the second OCT B-scan at the second cross-sectional position;

sequentially obtaining first OCT B-scans at two or more additional cross-sectional positions after obtaining the first and second OCT B-scans at the first and second cross-sectional positions; and sequentially obtaining, after obtaining the first OCT B-scans at the two or more additional cross-sectional positions, the third OCT B-scan at the first cross-sectional position and a third OCT B-scan at the second cross-sectional position.

13. The method of claim 1, wherein the multiple OCTA images are generated based on respective pairs of the OCT B-scans at the same cross-sectional position.

14. A system for optical coherence tomography angiography (OCTA), the system comprising:
an optical coherence tomography (OCT) system;
a logic subsystem; and
a data holding subsystem comprising non-transitory machine-readable instructions stored thereon that are executable by the logic subsystem to:
obtain, via the OCT system, three or more OCT B-scans of a sample at each of a plurality of cross-sectional positions along a slow axis using a stepped scanning pattern on the slow axis, wherein to obtain the OCT B-scans includes to:
obtain a first OCT B-scan, a second OCT B-scan, and a third OCT B-scan at a first cross-sectional position of the cross-sectional positions, wherein a first time period between the first and second OCT B-scans is different than a second time period between the second and third OCT B-scans, and wherein a third time period between the first and third OCT B-scans is different than the first and second time periods; and
obtain, via the stepped scanning pattern on the slow axis, at least one of the OCT B-scans at one or more other cross-sectional positions of the plurality of cross-sectional positions in between the first and second OCT B-scans or second and third OCT B-scans at the first cross-sectional position;
generate multiple OCTA images based on the three or more OCT B-scans at each of the plurality of cross-sectional positions; and
combine the multiple OCTA images to obtain a high dynamic range (HDR) OCTA image.

15. The system of claim 14, wherein to obtain the OCT B-scans includes to:
obtain the first OCT B-scan at the first cross-sectional position;
obtain a first number of the OCT B-scans at the one or more other cross-sectional positions after the first OCT B-scan is obtained;
obtain the second OCT B-scan at the first cross-sectional position after the first number of OCT B-scans is obtained;
obtain a second number of OCT B-scans at one or more additional cross-sectional positions, of the plurality of cross-sectional positions, after the second OCT B-scan is obtained, wherein the second number is different than the first number; and
obtain the third OCT B-scan at the first cross-sectional position after the second number of OCT B-scans is obtained.

16. The system of claim 15, wherein the first number of OCT B-scans is one, and wherein the second number of OCT B-scans is greater than one.

17. The system of claim 16, wherein the second number of OCT B-scans is 3.

18. The system of claim 15, wherein the OCT B-scans are obtained using bidirectional scanning.

19. The system of claim 14, wherein to obtain the OCT B-scans includes to:
obtain the first OCT B-scan at the first cross-sectional position;
obtain the second OCT B-scan at the first cross-sectional position after the first OCT B-scan is obtained;
obtain the one or more OCT B-scans at the one or more other cross-sectional positions after the first and second OCT B-scans are obtained; and
obtain the third OCT B-scan at the first cross-sectional position after the one or more OCT B-scans at the one or more other cross-sectional positions are obtained.

20. The system of claim 19, wherein the first and second OCT B-scans are obtained sequentially.

21. The system of claim 20, further comprising performing a flyback of a scanner between obtaining the first and second OCT B-scans.

22. The system of claim 19, wherein the obtaining one or more OCT B-scans at the one or more other cross-sectional positions comprises obtaining one OCT B-scan at a second cross-sectional position that is adjacent to the first cross-sectional position along the slow axis.

23. The system of claim 19, wherein the OCT B-scans are obtained using raster scanning.

24. The system of claim 19, wherein the one or more OCT B-scans at the one or more other cross-sectional positions are a first number of OCT B-scans, and wherein the instructions are further to cause the logic subsystem to obtain a second number of the OCT B-scans at one or more additional cross-sectional positions, of the plurality of cross-sectional positions, after the first OCT B-scan is obtained and before the second OCT B-scan is obtained.

25. The system of claim 14, wherein the OCT B-scans are obtained via bi-directional scanning, wherein the at least one of the OCT B-scans at one or more other cross-sectional positions includes a first OCT B-scan and a second OCT B-scan at a second cross-sectional position, and wherein to obtain the OCT B-scans includes to:
sequentially obtain the first OCT B-scan at the first cross-sectional position and a first OCT B-scan at the second cross-sectional position;
sequentially obtain, after obtaining the first OCT B-scans at the first and second cross-sectional positions, the second OCT B-scan at the first cross-sectional position and the second OCT B-scan at the second cross-sectional position;
sequentially obtain first OCT B-scans at two or more additional cross-sectional positions after the first and second OCT B-scans at the first and second cross-sectional positions are obtained; and
sequentially obtain, after the first OCT B-scans at the two or more additional cross-sectional positions are obtained, the third OCT B-scan at the first cross-sectional position and a third OCT B-scan at the second cross-sectional position.

26. The system of claim 14, wherein the multiple OCTA images are generated based on respective pairs of the OCT B-scans at the same cross-sectional position.

* * * * *